United States Patent [19]

Milch et al.

[11] Patent Number: 4,488,912
[45] Date of Patent: Dec. 18, 1984

[54] PREPARATION OF HIGH FRUCTOSE SYRUPS FROM CITRUS RESIDUES

[75] Inventors: Robert A. Milch, Baltimore; Patricia Guerry-Kopecko, Rockville; Carol Koeble-Smith, Germantown; Edward M. Sybert, Ellicott City, all of Md.

[73] Assignee: IGI Biotechnology, Inc., Md.

[21] Appl. No.: 405,037

[22] Filed: Aug. 4, 1982

[51] Int. Cl.³ .......................... C13K 1/00; C13B 1/00; C11G 9/02; C12P 19/02
[52] U.S. Cl. .......................... 127/41; 127/43; 127/46.1; 127/46.2; 127/56; 210/772; 210/790; 426/15; 426/48; 435/99; 435/105; 435/137; 435/164; 536/128
[58] Field of Search .......... 127/41, 46.1, 46.2, 127/43, 55, 56, 6; 260/236.5, 236.6; 536/125, 128, 127; 435/94, 99, 105, 137, 144, 157, 161, 164, 174; 426/15, 48, 51, 52, 53, 489, 490, 495, 651; 210/768, 772, 790; 424/195, 356

[56] References Cited

U.S. PATENT DOCUMENTS

| | | | |
|---|---|---|---|
| 1,465,459 | 8/1923 | Walton | 435/105 |
| 2,016,584 | 10/1935 | Ash et al. | 127/46.1 X |
| 2,125,846 | 8/1938 | Laughlin | 210/772 X |
| 2,276,420 | 3/1942 | Rosenfeld | 435/164 X |
| 2,440,029 | 4/1948 | Tabor et al. | 260/236.5 |
| 2,776,278 | 1/1957 | Birds | 260/236.6 |
| 2,949,389 | 8/1960 | Murtaugh et al. | 127/46.1 X |
| 3,313,655 | 4/1967 | Miyahara et al. | 127/41 X |
| 3,476,570 | 11/1969 | Moustafa | 210/772 X |
| 4,130,556 | 12/1978 | Wachter et al. | 260/236.5 |
| 4,242,145 | 12/1980 | Muller et al. | 127/41 |
| 4,332,622 | 6/1982 | Hohnerlein et al. | 127/41 |
| 4,356,195 | 10/1982 | Kahn et al. | 435/105 X |

FOREIGN PATENT DOCUMENTS

| | | | |
|---|---|---|---|
| 2477177 | 9/1981 | France | 127/43 |
| 57-102190 | 6/1982 | Japan | 435/164 |

Primary Examiner—Kenneth M. Schor
Attorney, Agent, or Firm—Haight & Associates

[57] ABSTRACT

The sugar content of citrus press liquor is enhanced by separating citrus solids, extracting fructose, glucose, and sucrose from the solids, and recombining the aqueous extract to increase the sugar content thereof. By inversion of the sucrose present in the sugar-enhanced press liquor, a high fructose syrup can be readily obtained which appears indistinguishable from high fructose corn syrup. When separation is effected by centrifugation, a colloidal phase is formed from which limonene and biocidal flavanoids can be extracted, resulting in a press liquor suitable for fermentation to alcohol. The solid residue remaining after extraction can also be recycled with the remaining press cake.

12 Claims, 2 Drawing Figures

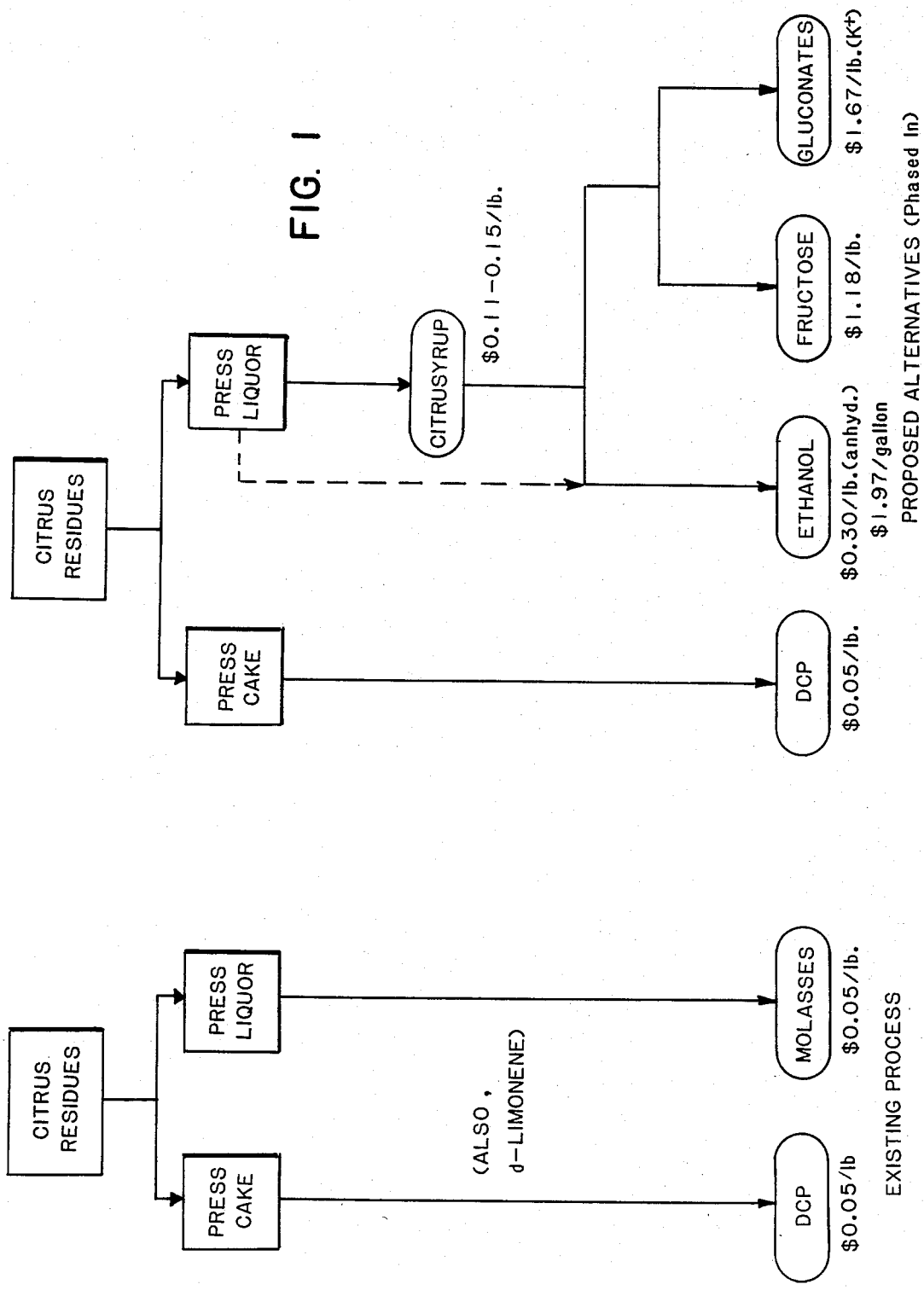

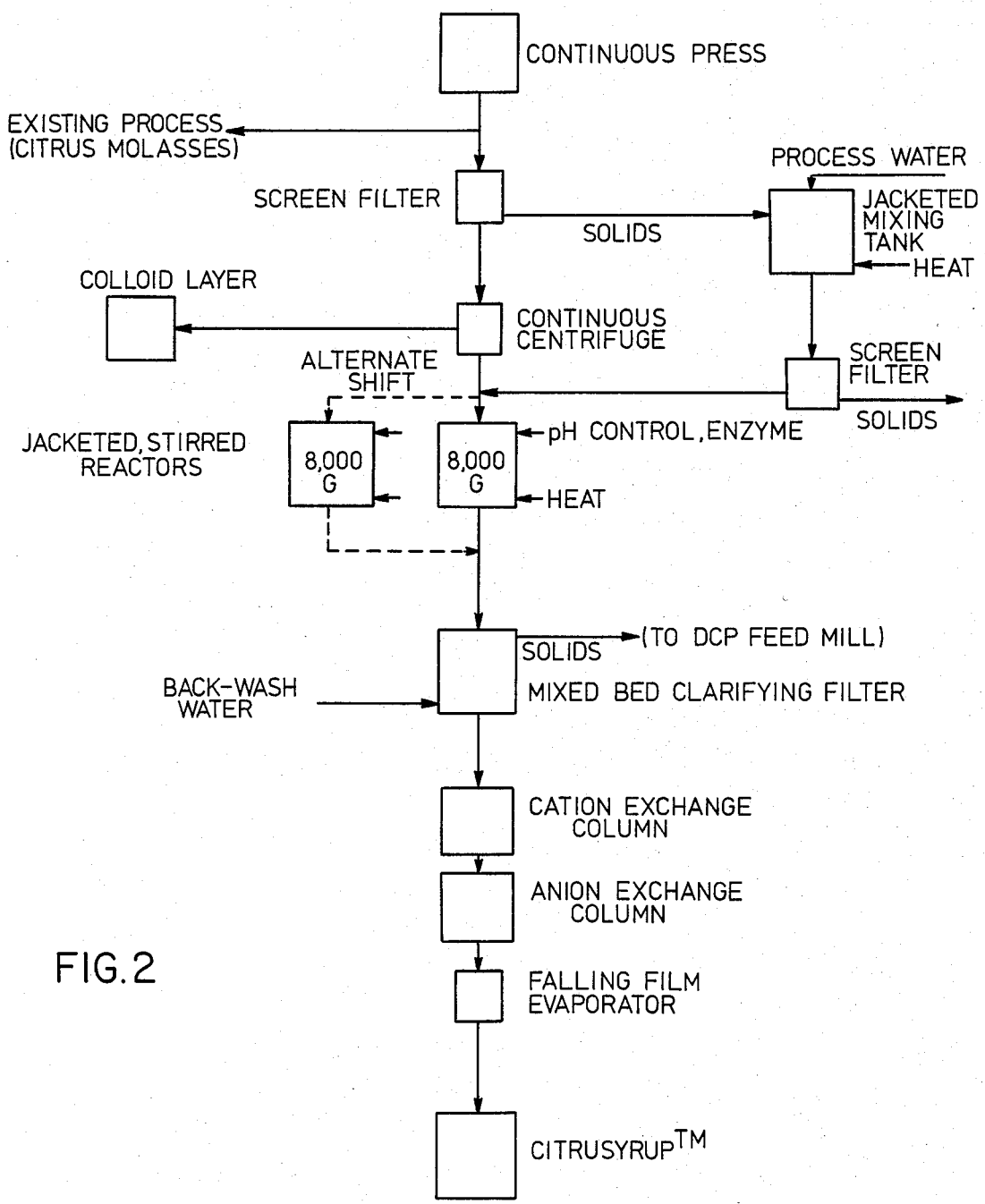

PREPARATION OF HIGH FRUCTOSE SYRUPS FROM CITRUS RESIDUES

DESCRIPTION OF THE INVENTION

1. Technical Field of the Invention

This invention relates to a process for increasing sugar levels in citrus press liquor and for obtaining a concentrate containing high sugar levels from citrus press liquor. The sugar enhanced citrus press liquor of the present invention can be concentrated and the sugar inverted to give a syrup having a high level of fructose.

2. Background Art

One of the problems associated with the growth of citrus production has been the disposal of peel residues as well as the rag, juice sacs and seeds from citrus fruit. Various approaches to solving such problems have been summarized by J. W. Kesterson and R. J. Braddock in "By-products and Specialty Products of Florida Citrus", Fla. Agr. Exp. Sta. Bul. 784 (December 1976), the contents of which are incorporated by reference herein. As used herein, the term "citrus" refers to any member of the genus Citrus, including but not limited to the orange, grapefruit, tangerine, tangelo, lemon, lime, citron, and mandarin. Most of the waste residue from commercial juice extractors is shredded, limed, cured and pressed into press liquors and press cakes which are then processed independently. Cured press cakes are dried in a feed mill to yield "dried citrus pulp" (DCP), from which cattle and swine feed pellets are prepared. The press liquors are concentrated in multiple effect heat evaporators to yield citrus molasses, while d-limonene is obtained from the condensate. However, present commercial processes still discard valuable and important components from citrus fruit processing operations.

B. R. Breslau et al. describe in Trans. Citrus Eng. Conf. ASME Lakeland 22: 53 (1976) a process for recovering the soluble constituents of citrus press liquor by screening and ultrafiltration of the resultant filtrate with hollow fibers to separate solids and oil suspensions from the citrus press liquor and produce a permeate faction containing dissolved sugars. The ultrafiltration retenate fraction containing suspended solids (including finely divided "shards" of peel, pulp, and seed residues present in the screened liquor) is considered waste to be used as conventional animal feed or to produce molasses.

A general object of this invention is to provide a process for separating and recovering valuable products from solid waste material present in citrus press liquor.

A principal object of this invention is to provide a process for recovering sugars from the shards present in citrus press liquor.

Another object of this invention is to provide a process for purifying sugar extracts obtained from citrus waste material to yield mixtures of non-reducing sugars as well as glucose and fructose.

A more particular object of this invention is to provide a process for preparing high fructose syrups, comparable to commercial high fructose corn syrup sweeteners, from citrus waste materials.

Another principal object of this invention is to provide a process for recovering limonene and other antimicrobial materials from citrus press liquor.

A further object of this invention is to provide citrus press liquor which is substantially free of such antimicrobial materials, thereby permitting its use as a feedstock in microbiological processes.

Yet another object of this invention is to provide a process for recovering the solid residues of sugar-extracted shards obtained from citrus press liquor for use in the production of dried citrus pulp.

Upon study of the specification, drawings and appended claims, further objects, features and advantages of the present invention will become more fully apparent to those skilled in the art to which this invention pertains.

DISCLOSURE OF THE INVENTION

Briefly, the above and other objects of this invention are obtained in one aspect thereof by providing a process for increasing the sugar content of citrus press liquor which comprises separating a major portion of finely divided shards consisting essentially of suspended peel, pulp and seed citrus solids from citrus press liquor and extracting fructose, glucose, and sucrose present in the separated solids. The aqueous extract is preferably recombined with citrus press liquor which is substantially free of citrus solids to increase the sugar contents thereof by at least 20 percent, generally 30-40 percent by volume.

The present invention is based in part upon the discovery that citrus press liquor, which is obtained by pressing waste citrus material such as peels, pulp and seeds, contains at least three distinct and easily separable physical and chemical phases. Approximately 50 percent (by wet weight) of the press liquor is composed of small insoluble fragments or "shards" which are not removed by existing processes for separating press cake from press liquor. In accordance with this invention, press liquor is treated by separation techniques such as ultrafiltration or centrifugation to recover these shards. The shards are then suspended in a hot aqueous solvent, preferably water, to produce a sugar-enhanced aqueous extract which is recombined with the press liquor supernatant from the initial separation treatment to increase the sugar content thereof. The resultant sugar-enhanced citrus press liquor typically contains solubilized hemicelluloses and pectins along with fermentable sugars at a level over 20 percent greater than initially present in the press liquor starting material. Approximately 95 percent of these sugars are represented by the disaccharide sucrose and the C6 reducing monosaccharides fructose and glucose.

When the initial crude citrus press liquor is centrifuged, separation of the press liquor into three distinct phases occurs. The top phase is a bright yellow or yellow-green colloidal layer which generally comprises 1-5 percent of the total volume and contains, among other components, d- and d,l-limonene. The middle layer is an aqueous phase containing dissolved sugars together with stabilized hemicelluloses and pectins present in the original press liquor, and its color varies from pale yellow to pale brown depending on the pH; generally, a lighter color reflects a lower pH. The third phase is a solid pellet comprising the shards. The amount recovered varies from batch to batch of citrus press liquor, but is generally about 5-10 g/100 ml. Alternatively, the solids can be separated from the press liquor by ultra-filtration, e.g. as described by R. J. Braddock et al, J. Food Sci 47(3): 946-948 (1982); however, centrifugation is presently preferred as it readily separates the three distinct phases for immediate subsequent treatment.

It has been found that heating these shards suspended in an aqueous solvent for a brief period of time, preferably in a volume of solvent roughly corresponding to the original volume of press liquor for 10–15 minutes at 65°–85° C., then cooling, separating the shard residues and recombining the aqueous extract with the separated press liquor line consistently increases the hexose content of the press liquor by at least 20 percent, typically 30–40 percent or more on a volume basis, thereby returning a substantial amount of sugar to the press liquor line.

The solid material or shards, remaining after heating in water to separate the additional sugar components, can be dried and processed for animal feed if desired. Adding the extracted shard residues, consisting essentially of water-insoluble pectins, celluloses, and hemicelluloses, back to the press cake line increases the solids content thereof by at least 10 percent, typically 15–20 percent or more on a dry weight basis. This represents a substantial additional yield of dried citrus pulp from materials which have otherwise been lost in the citrus molasses line.

While the aqueous solution containing glucose, fructose, and sucrose can be independently inverted, it is more economical to return this solution to the press liquor line for a single step inversion of the sucrose present in both solutions. 95 percent of the sugars present in the aqueous extract are fructose, glucose, and sucrose, the latter being susceptible to inversion, e.g. by treatment with invertase according to techniques well known in the art such as described in U.S. Pat. No. 2,126,947, to yield a 50:50 mixture of glucose and fructose.

Inversion can take place at any point in the process subsequent to enhancement of the sugar level in the press liquor by addition of the aqueous shards extract. Sucrose inversion is generally carried out by adding invertase in either free or immobilized form to the sugar-enhanced press liquor and permitting inversion to occur over about a 1–2 hour period at a temperature of about 60° C. and a pH of about 4–5, preferably about 4.5, at which pH it has a yellow rather than brown color. At the end of this period the temperature is elevated (about 80° C.) or the pH raised (to about 7–8) sufficiently to inactivate the enzyme. Following neutralization to pH 7.5, the color of the inverted press liquor becomes light brown. There is usually some precipitatant or flocculant formed following incubation, which appears to be pectin, cellulose, and hemicellulose.

To avoid cloudiness, the inverted press liquor supernatant should be briefly heated to boiling or to a temperature within about 25° C. of its boiling point, e.g. to about 80°–100° C. for about 10–20 minutes. This heating produces additional flocculant precipitate containing finely divided and suspended solids which were not removed during the previous separation procedures and which may cause cloudiness in the sugar-enhanced press liquor if not removed. It has not yet been determined whether such treatment of the filtrate is necessary to similarly prevent cloudiness when the shards are separated by ultrafiltration, but it appears that this would depend on the details of the ultrafiltration process employed.

Following this heating procedure, the press liquor can be subjected to additional procedures to achieve further clarification and to produce a clear supernatant fluid having a golden color. These additional procedures include but are not limited to further centrifugation, filtration, and solvent extraction.

Optionally, additional solids from the supernatant press liquor can be removed at any point by means of extraction with a volatile alcohol, preferably a lower alkanol, e.g. methanol. Approximately equal volumes of methanol and supernatant press liquor are mixed together, which causes additional flocculant material to separate. Additional centrifugation separates the flocculant solids and gives a further clarified supernatant press liquor. Residual alcohol can be removed by evaporation until no odor of alcohol persists in the press liquor, and the separated flocculant material can be recycled back to the press cake line. Clarification can also be accomplished by using a series of filtration steps, e.g., using filters, sand, charcoal, and diatomaceous earth.

Filtration through a sand bed, e.g. of 18–30 mesh, is a convenient method for removing the flocculated material and other solids which are present at this stage. Preferably, the first and last portions of the effluent are discarded and the column washed with water. The effluent from which solids have been removed should be cloudy and have a golden yellow color.

Activated charcoal can then be used to remove solids, proteins, and coloring agents. Vacuum filtration through activated charcoal on filter paper is convenient and fairly rapid, yielding a filtrate which is clear and yellow and may contain charcoal particles.

Diatomaceous earth filtration can then be used to remove additional solids and coloring agents, again preferably by vacuum filtration through a bed of diatomaceous earth on a filter pad. The filtrate at this stage is clear and light yellow.

If desired, further solids removal can be achieved by ultrafiltration, e.g. through a Millipore 0.45μ filter. The solution should filter easily and the filtrate be a clear, pale yellow.

Still further clarification and purification of the press liquor following removal of the colloidal layer and solid components can be accomplished using ion exchange techniques. The inverted press liquor is first reacted with a strongly acidic cation exchange resin such as Dowex 50WX2 (H+ form) to remove cations and various color components from the press liquor. Other strongly acidic ion exchange resins of suitable mesh can be employed in place of Dowex 50 WX2, e.g. Rohm and Haas IR-116 and IR-118; Ionac C-298; Mitsubishi SK-102 or SK-103; Permutit-Zeocarb 225; and BioRad AG 50W-X2. Following this treatment, the pH of the press liquor is less than 1, and it should be clear and very pale yellow in color.

The inverted press liquor is then reacted with a strongly basic anion exchange resin such as BioRad AG1-X8 (Cl− form) to remove anions and additional color components. Comparable strongly basic anion exchange resins can be used in place of BioRad Ag1-X8, e.g. Dowex 1-X8 (SBR); Rohm and Haas IRA-400; Ionac ASB-1; Mitsubishi SA-100; and Permutit-Zeolit FF. The final solution obtained should be clear, colorless, and odorless, but may have a slightly bitter taste due to the acetic acid of the column.

After these procedures are complete, the final concentration of sugars generally ranges from 25–35 mg/ml for fructose and 30–37 mg/ml for glucose. The inverted sugar-enhanced press liquor can be concentrated to a 10 to 15 fold level using a thin film evaporator at moderate temperatures of about 50° C. to yield a final product which is a viscous, clear and colorless liquid.

The ratio of these sugars in citrus press liquor almost precisely equals their ratio in currently marketed "high fructose syrups" which have been isolated from corn (high fructose corn syrup or HFCS) and certain other agricultural products, which are sweeteners of commercial importance in the soft drink and other industries. The concentration of these sugars from citrus press liquor can be easily increased 10-15 fold to that of high fructose syrups by thin film and other evaporation techniques which do not require large amounts of energy. The resultant product is an approximately 50:50 solution of fructose and glucose which appears virtually indistinguishable from commercial high fructose syrups having a bulk selling price several fold greater than the animal feed or molasses which has previously been prepared from this material. Furthermore, this solution can, by techniques known to those skilled in the art, be easily and rapidly converted into pure fructose solutions and crystals and a precipitate of gluconic acid salts, having current bulk selling prices approximately an order of magnitude greater than even HFCS.

While presently preferred as a method for preparing high fructose syrups, the sugar-enhanced press liquor obtained in accordance with the present invention, whether concentrated or not, can be subsequently treated in various ways to yield valuable and important products. Examples include but are not limited to additional treatment using glucose oxidase to oxidize the glucose component to gluconic acid and precipitate gluconates, yielding pure fructose; use as a feedstock for ethanol fermentation or for the fermantation production of lactic acid and citric acid, as has been described by Kesterton et al.; use of the sugar-enhanced press liquor in the production of 2,3 butylene glycol by Aerobacter, as described by S. K. Long and R. Patrick in Applied Microbiology 9: 244-248 (1961); etc.

The colloidal phase of the press liquor can be separated from the press liquor to yield limonene and other biologically active compounds. Separation of the colloidal phase from the press liquor is preferably carried out in accordance with the present invention by centrifuging the residual press liquor either prior to or subsequent to removal of the shards.

The colloidal layer, which constitutes a distinct micellar or emulsion phase, can be separated and isolated by centrifugation from the remaining press liquor only after the peel shards have been removed. This layer has been found to contain, inter alia, limonene and at least two additional components, at least one of which appears to possess the C6-C3-C6 flavanoid skeleton. The residual liquid phase of the press liquor is composed principally of solubilized hemicelluloses, pectins, and fermentable sugars, thereby providing a starting material for the production of ethanol according to known techniques.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

BRIEF DESCRIPTION OF DRAWINGS

The above and other objects, features, and advantages of the present invention will become more fully apparent to those skilled in the art to which this invention pertains upon consideration of the present specification and annexed drawings, wherein:

FIG. 1 schematically illustrates representative alternative citrus residue processing schemes; and FIG. 2 schematically illustrates pilot scale operation from the press liquor line.

BEST MODE FOR CARRYING OUT THE INVENTION

While the following Examples employed orange press liquor as a starting material, the processes illustrated thereby are equally applicable with appropriate modification as needed to press liquor from other citrus fruit.

EXAMPLE 1

Separation of Suspended Citrus Solids

Referring to the drawings, FIG. 1 gives the general process flow parameters of the presently preferred process. Further details are given in FIG. 2, a flow chart for a typical pilot scale operation. This assumes a pilot plant operation in which 1000 gallons per hour are processed, with the remaining press liquor being returned to conventional molasses processing.

Orange peel shards are recovered from a press liquor line using a gravity fed microscreen filter at ambient temperature (28° C.) and conveyed to a jacketed mixing tank. The residual press liquor containing the bright yellow colloidal layer (which represented about 2-3 percent of the liquid phase by volume) was collected from the filter and pumped into a continuous feed centrifugal separator. Three components were recovered: a lower density, bright yellow colloid; a higher density aqueous phase containing essentially the sugar values of the press liquor; and a solid "shards" pellet containing peel, pulp and seed residues.

The separated shards were conveyed first to a stirred reactor where they were heated in water for 10-20 minutes at 65°-85° C. to extract additional amounts of sugars. The shards were then screen filtered as before, and the water extract added to the press liquor in the stirred reactors. Remaining shards were conveyed to the feed mill to add weight and substance to dried citrus pulp products.

EXAMPLE 2

Sucrose Inversion

Press juices and the sugar-containing water extract from the shard mixing tank were pumped into a jacketed and temperature-controlled stirred reactor. Yeast invertase granules were then added to the reactor and the sucrose inversion reaction allowed to proceed at 60° C. for approximately 2 hours at controlled pH. At the end of the 2-hour reaction period, tank temperature was elevated to 85° C. for approximately 15 minutes to inactivate the enzyme and to precipitate soluble pectin and cellulose.

As shown in Table 1, there is little or nothing to be gained by adding invertase to the press liquors at any other step in the process. Adequate inversion was achieved by simply adding the invertase to the stirred reactors.

TABLE 1

| Procedure | Percent Sucrose | |
|---|---|---|
| (2 hours at 60° C.) | Inverted | Remaining |
| No invertase added | 0 | 100 |
| Invertase added directly to press juice | 100 | 0 |
| Invertase added before heating | 100 | 0 |
| Invertase added after heating but before mixed bed clarifying filter | 100 | 0 |

EXAMPLE 3

Purification

The inverted glucose and fructose solution from Example 2 was pumped to a mixed bed clarifying filter containing industrial grade filtration sand, activated charcoal, and diatomaceous earth layers in order to partially deodorize and decolorize the resulting glucose and fructose solution and to remove soluble contaminants and insoluble pectin and cellulose fines before passage through (first to Dowex-50 then to Dowex-1) deionizing columns. A water wash of this mixed bed clarifying filter was undertaken at the end of each reaction period and the wash returned to press cake line leading to the dried citrus pulp feed mill. The effluent leaving the deionizing columns was a clear, colorless, and odorless solution containing approxiately 10-15 grams of sugars per 100 ml. More than 95 percent of the sugar content was glucose and fructose. This solution was concentrated 10 to 15 fold to a solids level of 90-95 percent using a Rotovap thin film evaporator at 50° C. to give a clean, colorless, viscous product containing about 44 percent fructose and 48 percent glucose. The overall yield of the process in terms of solids was in excess of 95 percent, i.e. over 95 percent of the inverted glucose and fructose was recovered from the effluent emerging from the deionizing columns.

EXAMPLE 4

Gas Chromotography

Differences between the various materials involved in the process were studied and illustrated by gas chromatography. Four sugar "peaks" were demonstrated for both clarified citrus press liquor and for the hot water extract of citrus shards. These include the $\alpha$- and $\beta$-anomers of glucose, the $\alpha$- and $\beta$-anomers of fructose, a sucrose peak, an unknown peak which behaves like mannoheptulose, and a maltose peak, the latter being an internal standard used for analytical purposes only.

The only difference from the reference sugar feedstock was the complete absence of a sucrose peak in the process material which demonstrated the presence only of the $\alpha$- and $\beta$-anomers of fructose, the $\alpha$- and $\beta$-anomers of glucose, and a sugar which behaves chromatographically like mannoheptulose.

EXAMPLE 5

Comparison With High Fructose Corn Syrup

The chromatographs and chemical proportions of fructose and glucose in the process material were compared with commercial preparations of High Fructose Corn Syrup (HFCS). The only difference between the reference material and the process material was the absence of the presumed mannoheptulose sugar in the reference preparations. The proportions of sugars in the process material and the reference material were virtually identical, as illustrated in Table 2:

TABLE 2

| | Proportion of Sugars in HFCS and Process Material | | |
|---|---|---|---|
| | Percent | | |
| Material | Fructose | Glucose | Other Sugars |
| Isomerose $^R$ 100 | 43 | 56 | 6 |
| Isomerose $^R$ 500 | 55 | 41 | 4 |
| Process Material | 47 | 49 | ~4 |

EXAMPLE 6

Chemical Analysis

Further chemical analysis was conducted on the process material after inversion according to Example 2. Some protein material occasionally remained in an order of magnitude comparable to that usually encountered in the commercial HFCS preparations. This appears to be a function of pH and of the effectiveness of the mixed bed clarifying filter in removing residual amounts of invertase protein.

Depending upon the extent of evaporation, the solids content after inversion can be made to vary from 50-95 percent solids, and correspondingly 5-50 percent moisture content, as desired. The dry basis composition was 99+ percent carbohydrate with an ash content of less than 0.05 percent. The process material was almost entirely indistinguishable from high fructose syrups of corn or other agricultural origin. The only detected difference was the presence of the unknown sugar (presumably mannoheptulose), comparable to the "other saccharides" component found in commercial isomerose and other high fructose syrup preparations.

EXAMPLE 7

Growth Inhibition by Colloidal Layer

Equal volumes (100 ml each) of raw citrus press liquor were centrifuged at 6000 rpm to give three distinct layers previously described. The colloidal layer of one batch was removed by skimming and filtering through cheesecloth and the middle aqueous phase decanted from the shard pellet. The colloidal layer of a control batch was not removed, but decanted along with the aqueous phase from the shards. These aqueous phases with and without the colloidal phase were diluted 1:1 with water, sterilized by autoclaving, and compared for their ability to support the growth of Saccharomyces cerevisiae (ATCC 4126). The aqueous phase with the colloidal layer did not support growth of the yeast, and viable counts of the organisms dropped upon incubation. The aqueous phase without the colloidal layer supported growth of the yeast to allow direct ethanol fermentation.

Similar experiments demonstrated that a component in the colloidal layer inhibited the growth of Clostridium thermohydrosulfuricum (ATCC 33,223) used to convert sugar to alcohol, and of Clostriduim thermocellum (ATCC 27,405) used to break down cellulose into sugars and of Gluconobacter oxydans subs. suboxydans (ATCC 621). However, antibacterial activity of the colloidal layer was selective as evidenced by the fact that it did not similarly inhibit Lactobacillus bulgaricus (ATCC 11,842), Lactobacillus casei, subp. rhamnosus (ATCC 7,469), or Lactobacillus lactis (ATCC 12,315). It appears that this selective inhibition is due to the presence of limonene and/or flavanoids in the colloidal layer, which become gummy when dried.

EXAMPLE 8

Fermentation

Citrus press liquor without the colloidal layer was prepared as described in Example 7 and successfully used as a feedstock for an ethanol fermentation using *Saccharomyces cerevisiae* (ATCC 4126). The fermentation was complete after a 36 hour incubation at 30° C.

EXAMPLE 9

Recovery of Citrus Terpenes

The bright yellow colloidal material recovered from the citrus press liquor during the continuous separation of Example 1 was distilled under vacuum and mild heat (60° C.) and the distillate was recovered from the vapor phase using a water cooled condensor operating at 18° C. This distillate was a colorless liquid having a distinct citrus aroma and was shown by mass spectral predominately limonene.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

Industrial Applicability

The process described herein greatly increases the economic value of citrus press liquors which have heretofore been used as a source of citrus molasses and dry citrus pulp animal feed of low economic value. Furthermore, by removing fermentation inhibition components in the colloidal layer, citrus sugars obtained therefrom can now be used as a fermentation feedstock.

What is claimed is:

1. A process for recovering a plurality of useful products from a citrus press liquor line from which a citrus press cake and screenable solids have been removed, which process comprises:
   (A) centrifuging the screen filtered press liquor to form (i) 1 to 5 percent by volume of an upper colloid phase consisting essentially of limonene-containing biocidally active materials from said press liquor, (ii) a middle aqueous phase which is substantially free of said biocidally active materials and consists essentially of the dissolved sugars and soluble polymeric carbohydrates from said press liquor, and (iii) a solid phase consisting essentially of citrus fragments and shards from said press liquor;
   (B) separating the colloid phase (i) from the aqueous phase (ii) and the solid phase (iii) and recovering the biocidally active materials from the separated colloid phase:
   (C) separating the solid phase from the aqueous phase;
   (D) extracting fructose, glucose, and sucrose from the separated citrus fragments and shards of the solid phase by suspending the separated solid phase in a volume of water at 65–85 degrees C. roughly corresponding to the original volume of said centrifuged press liquor for about 10 to 15 minutes;
   (E) separating the water-insoluble material of the solid phase from step (C) and combining it with a press cake from which citrus press liquor has been separated to increase the solids content thereof by at least 10 percent on a dry weight basis; and
   (F) combining the separated aqueous extract from step (D) with the aqueous phase from step (C) to increase the hexose content of said aqueous phase by at least 20 percent by volume.

2. A process according to claim 1, wherein the fructose, glucose, and sucrose equivalent of the citrus press liquor is increased to a concentration comparable to that of high fructose corn syrup.

3. A process according to claim 2, further comprising inverting the extracted sucrose from step (C) to form substantially equimolar amounts of glucose and fructose.

4. A process according to claim 3, wherein the citrus press liquor is treated with invertase following recombination with the aqueous extract from step (E).

5. A process according to claim 1, wherein the water-insoluble material from step (D) is further converted into dried citrus pulp.

6. A process according to claim 1, further comprising fermenting at least one sugar extracted in step (C).

7. A process according to claim 3, further comprising converting at least one of said sugars into a corresponding carboxylic acid or salt thereof.

8. A process according to claim 7, wherein glucose is converted into gluconic acid or a salt thereof, further comprising recovering fructose from the resultant solution.

9. A process according to claim 3, further comprising heating the inverted press liquor to about 80–100 degrees C. to form a flocculent precipitate and separating the precipitate from the inverted press liquor to prevent cloudiness therein.

10. A process according to claim 9, wherein the separated flocculent is combined with a press cake from which citrus press liquor has been separated.

11. A process according to claim 3, further comprising removing additional solids from the sugar-enhanced press liquor from step (D) by alcohol extraction after the separating of step (E).

12. A process according to claim 1, further comprising clarifying the inverted press liquor by sequential reaction with a strongly acidic, then a strongly basic, ion exchange resin.

* * * * *